(12) United States Patent
Steer

(10) Patent No.: US 6,627,585 B1
(45) Date of Patent: Sep. 30, 2003

(54) MOUSSE-FORMING SHAMPOO COMPOSITIONS

(75) Inventor: David Charles Steer, Wirral (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

(21) Appl. No.: 09/592,191

(22) Filed: Jun. 12, 2000

(30) Foreign Application Priority Data

Jun. 15, 1999 (GB) ............................................. 9913951

(51) Int. Cl.$^7$ ......................... C11D 17/00; A61K 7/075
(52) U.S. Cl. ....................... 510/120; 510/122; 510/128; 510/406; 424/47; 424/70.1; 424/70.12
(58) Field of Search ................................ 510/119, 120, 510/122, 128, 406; 424/47, 70.1, 70.12

(56) References Cited

U.S. PATENT DOCUMENTS

| | | | |
|---|---|---|---|
| 3,294,725 A | 12/1966 | Findlay et al. | |
| 3,360,491 A | 12/1967 | Axon | |
| 4,009,256 A | 2/1977 | Nowak, Jr. et al. | |
| 4,152,416 A | 5/1979 | Spitzer et al. | |
| 4,574,052 A * | 3/1986 | Gupte et al. | 510/120 |
| 4,871,530 A * | 10/1989 | Grollier et al. | 424/47 |
| 5,180,584 A * | 1/1993 | Sebag et al. | 424/401 |
| 5,456,863 A * | 10/1995 | Bergmann | 510/122 |
| 5,573,709 A * | 11/1996 | Wells | 510/122 |
| 5,580,550 A * | 12/1996 | Gough et al. | 424/70.11 |
| 5,714,446 A * | 2/1998 | Bartz et al. | 510/119 |
| 5,977,038 A * | 11/1999 | Birtwistle et al. | 510/122 |
| 6,037,407 A * | 3/2000 | Derian et al. | 524/837 |
| 6,110,451 A * | 8/2000 | Matz et al. | 424/70.16 |
| 6,180,576 B1 * | 1/2001 | Melby et al. | 510/121 |

FOREIGN PATENT DOCUMENTS

| | | |
|---|---|---|
| EP | 0460683 | 12/1991 |
| EP | 0498119 | 8/1992 |
| EP | 0567326 | 10/1993 |
| EP | 0674898 | 10/1995 |
| EP | 0818190 | 1/1998 |
| WO | 95/05158 | 2/1995 |
| WO | 95/22311 | 8/1995 |
| WO | 95/23581 | 9/1995 |
| WO | 96/32919 | 10/1996 |
| WO | 97/14396 | 4/1997 |
| WO | WO-97/20626 A1 * | 6/1997 |
| WO | 98/19654 | 5/1998 |
| WO | 99/32070 | 7/1999 |
| WO | 00/64404 | 11/2000 |

* cited by examiner

Primary Examiner—Lorna M. Douyon
(74) Attorney, Agent, or Firm—Michael P. Aronson

(57) ABSTRACT

A mousse-forming cleansing shampoo composition having improved conditioning performance comprising:

(A) a foamable concentrate comprising:
   (i) at least one surfactant;
   (ii) dispersed particles of a water-insoluble conditioning agent having a particle size of 1 micron or greater;
   (iii) an aqueous carrier; and
(B) an aerosol propellant.

10 Claims, No Drawings

MOUSSE-FORMING SHAMPOO COMPOSITIONS

FIELD OF THE INVENTION

The present invention relates to mousse-forming shampoo compositions. More particularly, the invention relates to mousse-forming shampoo compositions which include dispersed particles of a conditioning agent such as a silicone or oily material and which impart good conditioning benefits to hair and/or skin.

BACKGROUND AND PRIOR ART

Mousses are a particularly convenient and pleasant-to-use product form for hair treatment formulations. The product is generally applied to the user's hand, where it forms a creamy foam which can be easily worked through the hair.

Such mousses have found widespread use in the context of hair styling products. The conventional hair styling mousse generally utilises a water soluble hair styling polymer, water, possibly a conditioning agent, an emulsifier, aesthetic agents and an aerosol propellant. The mousse is typically applied to hair dampened with water, spread through the hair and allowed to dry, giving a temporary set which can be removed by water or by shampooing.

It would be desirable to provide a rinse-off surfactant-based cleansing shampoo in a mousse product form. Consumers appreciate the ease of dispensing and application of a mousse, and the way it can be worked through the hair without getting into the eyes. The latter would be particularly advantageous in the context of formulations based primarily on cleansing surfactants which can sometimes be harsh and irritating to the eyes. However, prior art systems of this type have not achieved much success, largely because the level of conditioning they deliver is insufficient for many people.

The problem stems mainly from the fact that the shampoo in the dispenser must dispense easily. This requirement is generally incompatible with shampoos which incorporate a significant amount of water-insoluble conditioning agents.

For example, silicones are highly desirable water-insoluble conditioning agents for incorporation into shampoos, as is well documented in the literature. However, the problem arises that the usual viscosity level required of the shampoo base in order to prevent the silicone from separating in the formulation is generally too high for effective dispensing of the shampoo from an aerosol formulation. This is manifest as a dispensing problem—the product will tend to dispense slowly and unevenly.

WO95/05158 describes an anionic surfactant based aerosol shampoo formulation. The exemplified formulations do not contain any silicones or other water-insoluble conditioning agents.

We have now found that rinse-off surfactant-based cleansing shampoo compositions can be formulated which deliver excellent conditioning performance from a mousse product form. Surprisingly, compositions of the invention are simple to formulate and can be dispensed easily from an aerosol can simply by agitation of the can where necessary.

SUMMARY OF THE INVENTION

The present invention provides a mousse-forming cleansing shampoo composition having improved conditioning performance comprising:

(a) a foamable concentrate comprising:

(i) at least one surfactant;
(ii) dispersed particles of water-insoluble conditioning agent having a particle size of one micron or greater;
(iii) an aqueous carrier; and (b) an aerosol propellant.

DETAILED DESCRIPTION AND PREFERRED EMBODIMENTS

Foamable Concentrate

The mousse-forming cleansing shampoo composition of the invention comprises a foamable concentrate and an aerosol propellant. The term "concentrate" will be used to refer to the liquid component of the shampoo composition other than a mousse-forming cleansing shampoo composition having improved conditioning performance comprising:

(A) a foamable concentrate comprising:
  (i) at least one surfactant;
  (ii) dispersed particles of a water-insoluble conditioning agent having a particle size of 1 micron or greater;
  (iii) an aqueous carrier; and
(B) an aerosol propellant. The term "mousse", as used herein, is the same as foam, and refers to the dispensed product unless otherwise specified.

In general, for optimum dispensability of the product, we have found that the viscosity of the foamable concentrate should not exceed 3000 cps.

The viscosity of the foamable concentrate suitably ranges from 1 to 3000, preferably from 10 to 2000, ideally from 100 to 1000 cps.

Viscosity is measured in the conventional manner using a rotary viscometer (Brookfield Viscometer, LVT type, Rotor No.3, 12 rpm after 30 sec. at 25 degrees C.).

In order to achieve such suitable viscosities as described above for the foamable concentrate, it is particularly preferred that the foamable concentrate be substantially free of crystalline suspending agents. By "substantially free" it is generally meant that the level of such agents be about 0.5% or less, preferably about 0.1% or less, ideally no more than about 0.05% by weight of the foamable concentrate.

Crystalline suspending agents include long chain (e.g. C8–C22) acyl derivative materials and long chain amine oxides, such as ethylene glycol long chain esters, alkanolamides of long chain fatty acids, long chain esters of long chain fatty acids, glyceryl long chain esters, long chain esters of long chain alkanolamides, and long chain alkyl dimethyl amine oxides. Common suspending agents of this type are ethylene glycol esters of C14–C22 fatty acids (e.g. ethylene glycol distearate), C16–C22 fatty acid alkanolamides (e.g. stearic monoethanolamide, stearic monoisopropanolamide), C16–C22 alkyl dimethyl amine oxides and N,N-dihydrocarbyl (C12–C22) amidobenzoic acid and salts thereof.

It may in some cases also be preferable, in order to achieve suitable viscosities as described above for the foamable concentrate, to incorporate therein a rheology modifier such as a thinner. Suitable thinners include polyethylene glycol (PEG), polypropylene glycol (PPG), sodium xylene sulphonate, sodium toluene sulphonate and urea. Preferred thinners are PEG 400 and PPG 400.

Conditioning Agent

The foamable concentrate comprises dispersed particles of a water-insoluble conditioning agent having a particle size of 1 micron or greater.

By "water insoluble" is meant is that the conditioning agent is not soluble in water (distilled or equivalent) at a concentration of 0.1 wt %, at 25° C. and pH 7.

Particle size may be measured by means of a laser light scattering technique, using a 2600D Particle Sizer from Malvern Instruments.

As used herein, the term "conditioning agent" includes any material which is used to give a particular conditioning benefit to hair and/or skin. For example, in shampoo compositions for use on the skin, materials such as moisturisers, essential oils, sun-protective or after-sun treatment materials, occlusive oils and the like may be used. In shampoo compositions for use on the hair, suitable materials are those which deliver one or more benefits relating to shine, softness, combability, wet-handling, anti-static properties, protection against damage, body, volume, stylability and manageability.

Preferred conditioning agents for use in compositions of the invention are selected from silicones, high molecular weight hydrocarbon materials, hair conditioning oily or fatty materials and mixtures thereof.

Silicones

Suitable silicones may be one or more polyalkyl siloxanes, one or more polyalkylaryl siloxanes, or mixtures thereof. The silicone is insoluble in the aqueous matrix of the foamable concentrate and so is present as dispersed particles.

The viscosity of the silicone itself preferably ranges from 10,000 cps to 5 million cps.

Suitable polyalkyl siloxanes include polydimethyl siloxanes which have the CTFA designation dimethicone, having a viscosity of up to 100,000 centistokes at 25 degrees C.

These siloxanes are available commercially from the General Electric Company as the Viscasil series and from Dow Corning as the DC 200 series. The viscosity can be measured by means of a glass capillary viscometer as set out further in Dow Corning Corporate Test Method CTM004 Jul. 20, 1970.

Also suitable is polydiethyl siloxane.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000 and specific examples include polydimethyl siloxane polymers, polydimethyl siloxane/diphenyl/methylvinylsiloxane copolymers, polydimethylsiloxane/methylvinylsiloxane copolymers and mixtures thereof.

Aminofunctional silicones which have the CTFA designation amodimethicone, are also suitable for use in the compositions of the invention, as are polydimethyl siloxanes having hydroxyl end groups (which have the CTFA designation dimethiconol).

The silicone materials described above are preferably incorporated in the foamable concentrate as a pre-formed aqueous emulsion. The average particle size of the silicone material in this emulsion, in the foamble concentrate, and in the fully formulated mousse shampoo composition is generally from 2 to 30 microns, preferably from 2 to 20 microns, more preferably 3 to 10 microns.

The pre-formed emulsion may be prepared by high shear mechanical mixing of the silicone and water, or by emulsifying the insoluble, non-volatile silicone with water and an emulsifier—mixing the silicone into a heated solution of the emulsifier for instance, or by a combination of mechanical and chemical emulsification. A further suitable technique for preparation of the emulsions is emulsion polymerisation. Emulsion polymerised silicones as such are described in U.S. Pat. No. 2,891,820 (Hyde), U.S. Pat. No. 3,294,725 (Findlay) and U.S. Pat. No. 3,360,491 (Axon).

Any surfactant materials either alone or in admixture may be used as emulsifiers in the preparation of the pre-formed silicone emulsions. Suitable emulsifiers include anionic, cationic and nonionic emulsifiers. Examples of anionic emulsifiers are alkylarylsulphonates, e.g., sodium dodecylbenzene sulphonate, alkyl sulphates e.g., sodium, lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic emulsifiers are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Typically, a pre-formed emulsion will contain around 50% of, silicone. Pre-formed emulsions are available from suppliers of silicone oils such as Dow Corning, General Electric, Union Carbide, Wacker Chemie, Shin Etsu, Toshiba, Toyo Beauty Co, and Toray Silicone Co. Examples are the material sold as DC2-1310 by Dow Corning (an emulsion of 60,000 cst dimethicone in nonionic surfactant), and the materials sold as X-52-1086, X-52-2127 and X-52-2112 by Shin-Etsu.

The silicone may be present in compositions of the invention as a single material or as a mixture of different silicones, e.g. having different particle sizes and/or functional groups.

The amount of silicone incorporated into the compositions of the invention depends on the level of conditioning desired and the material used. A preferred amount is from 0.01 to about 10% by total weight of silicone based on total weight of the foamable concentrate although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by total weight of silicone based on total weight of the foamable concentrate, is a particularly suitable level.

When the silicone is incorporated as a pre-formed emulsion as described above, the exact quantity of emulsion will of course depend on the concentration of the emulsion, and should be selected to give the desired quantity of silicone in the foamable concentrate.

High Molecular Weight Hydrocarbon Material

By "high molecular weight" is meant that the weight average molecular weight of the hydrocarbon material is at least 20,000. Suitably it ranges from 20,000 to 1,000,000, preferably 20,000 to 500,000, most preferably 40,000 to 200,000; these materials are especially effective for imparting improved fullness, body and volume to hair.

A preferred class of high molecular weight hydrocarbon materials are per-alk(en)yl hydrocarbon resins. These term "resin" is intended to encompass those materials which are solid or semi-solid at room temperature, as well as those which are liquids with high or moderate viscosities. The term does not cover low viscosity materials such as hydrocarbon oils.

EP 567 326 and EP 498 119 describe suitable peralk(en)yl hydrocarbon resins for imparting stylability and enhanced body to hair. Preferred per-alk(en)yl hydrocarbon materials are polymers of butene, isoprene, terpene and styrene, and copolymers of any combination of these monomers, such as butyl rubber (polyisobutylene-co-isoprene), natural rubber (cis-1,4-polyisoprene) and hydrocarbon resins such as mentioned in the Encyclopaedia of Chemical technology by Kirk and Othmer (3rd edition vol.8, pp 852–869), for example aliphatic and aromatic resins and terpene resins.

Especially preferred are polyisobutylene materials of the formula:

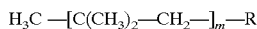

wherein m is 1-5000, preferably 2-2500, and R is:

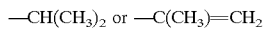

These materials are available from Presperse, Inc. under the PERMETHYL trade name, from Exxon Chemical under the VISTANEX trade name, and from BASF under the OPANOL trade name. Preferred examples include VISTANEX LM-MH and OPANOL B 15.

Suitable methods of making emulsions of particles of high molecular weight hydrocarbon materials such as polyisobutylene resins are described in EP 567 326 and EP 498 119. The process of EP 567 326 is preferred since it is a direct emulsification process with water and a suitable surfactant emulsifier which avoids the need to use a solvent or carrier which is capable of dissolving or dispersing the high molecular weight hydrocarbon material. Such solvents or carriers (e.g. low molecular weight hydrocarbons) can present safety hazards during processing and can destabilise the final formulations into which they are incorporated.

Emulsified high molecular weight hydrocarbon materials for use in hair treatment compositions of the invention generally have an average particle size in the foamable concentrate and in the fully formulated mousse shampoo composition of from 1 to 100 microns, more typically from 1 to 10 microns.

Suitable high molecular weight hydrocarbon emulsions for use in the invention are commercially available in a pre-emulsified form. This is particularly preferred since the pre-formed emulsion can be incorporated into the foamable concentrate by simple mixing.

An example of a suitable pre-formed emulsion is the material PIB 96/003 available from Basildon Chemical. This is an aqueous emulsion of the polyisobutylene resin OPANOL B 15 (ex BASF) with anionic and nonionic surfactant emulsifier.

The high molecular weight hydrocarbon material may be present in compositions of the invention as a single material or as a mixture of different high molecular weight hydrocarbon materials, e.g. of different molecular weights.

The amount of high molecular weight hydrocarbon material incorporated into the compositions of the invention depends on the level of fullness, body and volume enhancement desired and the specific material used. A preferred amount is from about 0.01 to about 2% by total weight of high molecular weight hydrocarbon material based on total weight of the foamable concentrate although these limits are not absolute. The lower limit is determined by the minimum level to achieve the fullness, body and volume enhancing effect and the upper limit by the maximum level to avoid making the hair unacceptably stiff. We have found that an amount of high molecular weight hydrocarbon material of from 0.2 to 0.5% by total weight of high molecular weight hydrocarbon material based on total weight of the foamable concentrate is a particularly suitable level.

When the high molecular weight hydrocarbon material is incorporated as a pre-formed emulsion as described above, the exact quantity of emulsion will of course depend on the concentration of the emulsion, and should be selected to give the desired quantity of high molecular weight hydrocarbon material in the foamable concentrate.

Hair Conditioning Oily or Fatty Material

Hair conditioning oily or fatty materials are preferred conditioning agents in compositions of the invention for adding shine to the hair and also enhancing dry combing and dry hair feel.

Suitable hair conditioning oily or fatty materials will generally have a viscosity at ambient temperature of about 3 million cst or less, preferably about 2 million cst or less, more preferably about 1.5 million cst or less. However, fatty materials which are solid at ambient temperature may also be suitable.

Advantageously, it is not necessary to emulsify the hair conditioning oily or fatty material in order to incorporate it successfully into mousse shampoo formulations according to the invention. In conventional (non-mousse) shampoo formulations, incorporation of oils can present difficulties since the emulsification process tends to cause dissolution of the oil in the shampoo surfactant and consequent disruption of surfactant mesophases. This problem is avoided in mousse shampoo formulations according to the invention, since if necessary they can simply be formulated as two-phase systems in which the oil phase is dispersible by agitation.

Suitable hair conditioning oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are liquid mixtures of hydrocarbons that are obtained from petroleum.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R' COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, and mixtures thereof.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di- and triglycerides.

Particularly preferred fatty esters are mono-, di- and triglycerides, more specifically the mono-, di-, and triesters of glycerol and long chain carboxylic acids such as $C_1$–$C_{22}$ carboxylic acids. A variety of these types of materials can be obtained from vegetable and animal fats and oils, such as coconut oil, castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Specific examples of preferred materials include cocoa butter and palm stearin.

The hair conditioning oily or fatty material may be present in compositions of the invention as a single material or as a blend.

The hair conditioning oily or fatty material is typically present at a level of from 0.05% to 10%, preferably from 0.2% to 5%, more preferably from about 0.5% to 3%, by total weight of oily or fatty material based on total weight of the foamable concentrate.

Mixtures of any of the above-described conditioning agents may also be used in compositions of the invention.

The total level of conditioning agent present in compositions of the invention is typically from 0.05% to 20%, preferably from 0.1% to 10%, more preferably from about 0.5% to 5%, by total weight of conditioning agent based on total weight of the foamable concentrate,.

Surfactant

The foamable concentrate comprises one or more surfactants, to provide a cleansing benefit. Surfactant may also be present as emulsifier for emulsified conditioning agents such as the silicones and high molecular weight hydrocarbon materials described above.

Further surfactant(s) will be present as an additional cleansing ingredient if sufficient for cleansing purposes is not provided as the emulsifier for the emulsified conditioning agent. This further cleansing surfactant may be the same surfactant as the emulsifier, or may be different.

Suitable emulsifiers are well known in the art and include anionic and nonionic surfactants. Examples of anionic surfactants used as emulsifiers are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Cleansing surfactants are typically selected from anionic, nonionic, amphoteric and zwitterionic surfactants, and mixtures thereof.

Suitable anionic cleansing surfactants for compositions of the invention include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates and acyl methyl taurates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionics include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, and sodium N-lauryl sarcosinate.

Nonionic cleansing surfactants suitable for use in shampoo compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include alkylpolyglycosides and mono- or di-alkyl alkanolamides. Examples of the latter nonionics include coco mono- or di-ethanolamide and coco mono-isopropanolamide.

Amphoteric and zwitterionic cleansing surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates and alkyl amidopropyl hydroxysultaines. Examples include lauryl amine oxide, cocodimethyl sulphopropyl betaine and preferably lauryl betaine, cocamidopropyl betaine and sodium cocamphopropionate.

The total amount of surfactant (including any used as emulsifier for the conditioning agent) is generally from 3 to 50%, preferably from 5 to 30%, more preferably from 10% to 25%, by total weight of surfactant based on total weight of the foamable concentrate.

Deposition Polymer

The foamable concentrate may contain a deposition polymer for the dispersed particles of conditioning agent. By "deposition polymer" is meant an agent which enhances deposition of the particles of conditioning agent from the shampoo composition of the invention onto the intended site during use, i.e. the hair and/or the scalp. The use of deposition polymers is particularly preferred in conjunction with the silicones and high molecular weight hydrocarbon materials described above.

The deposition polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic charge density of the deposition polymer, which is defined as the reciprocal of the molecular weight of a monomeric unit of the polymer containing one charge, should typically be at least 0.1 meq/g, preferably above 0.8 or higher. The cationic charge density should typically not exceed 4 meq/g. It is preferably less than 3 and more preferably less than 2 meq/g. The charge density can be measured using conductimetric analysis and should be within the above limits at the desired pH of use, which will in general be from about 3 to 9 and preferably between 4 and 8.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, alkyl vinyl pyridinium, and alkyl vinyl pyrrolidine salts. The alkyl portions of these monomers are preferably lower alkyls such as the C1–C3 alkyls, more preferably C1 and C2 alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1–C7 hydrocarbyls, more preferably C1–C3, alkyls.

The deposition polymer can comprise mixtures of monomer units derived from amine- and/or quaternary ammonium-substituted monomer and/or compatible spacer monomers.

Suitable deposition polymers include, for example: cationic copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in UK Application No. 9403156.4.

Other cationic deposition polymers that can be used include cationic guar gum derivatives, such as guar hydroxypropyltrimonium chloride (Commercially available from Celanese Corp. in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the deposition polymer is selected from cationic polyacrylamides and cationic guar derivatives. Particularly preferred deposition polymers are JAGUAR C13S with a cationic charge density of 0.8meq/g. Other particularly suitable materials include JAGUAR C15, JAGUAR C17 and JAGUAR C16 and JAGUAR C162.

The deposition polymer may be present in an amount of from 0.01 to 10%, preferably from 0.01 to 1%, more preferably from about 0.04 to about 0.5%, by weight of deposition polymer based on total weight of the foamable concentrate.

Aqueous Carrier

The foamable concentrate comprises an aqueous carrier, water forming the continuous phase in which the particles of water-insoluble conditioning agent are dispersed. Water is generally present in an amount of from about 20 to about 99% by weight based on total weight of the foamable concentrate.

Propellant

Compositions of the invention contain an aerosol propellant (B). This agent is responsible for expelling the other materials from the container and forming the mousse character.

The propellant gas can be any liquefiable gas conventionally used for aerosol containers. Examples of suitable propellants include dimethyl ether, propane, n-butane and isobutane, used singly or admixed. Other examples of propellants are nitrogen, carbon dioxide, compressed air and fluorohydrocarbons such as the material sold by Du Pont under the trade name DYMEL 152a.

The amount of the propellant gases is governed by normal factors well known in the aerosol art. For mousses the level of propellant is generally from about 3 to about 15%, optimally from about 4 to about 10%, by total weight of propellant based on total weight of the final mousse shampoo composition, for creamy foam and good sensory feel.

Optional Ingredients

Compositions of this invention may contain any other ingredient normally used in hair treatment formulations. These other ingredients may include hair styling resins, colouring agents, antifoam agents, proteins, moisturising agents, antioxidants, fragrances, antimicrobials and sunscreens. Each of these ingredients will be present in an amount effective to accomplish its purpose.

Packaging

Compositions of the invention are typically prepared by charging a suitable pressurisable container with the foamable concentrate, then sealing the container and charging it with propellant (B) according to conventional techniques.

The invention will now be illustrated by the following non-limiting Example.

All parts, percentages and proportions referred to are by weight based on total weight unless otherwise indicated.

EXAMPLES

Two shampoo formulations were made up using the following ingredients in the amounts stated.

| Ingredient | Comparative Example A (wt %) | Example 1 (wt %) |
|---|---|---|
| SLES 2EO | 14.0 | 13.3 |
| CAPB | 2.0 | 1.9 |
| Carbopol 980 | 0.4 | — |
| Sirius M70 mineral oil | 2.0 | 1.9 |
| Ethylene glycol distearate | 1.0 | — |
| PEG 6000 distearate | 2.5 | — |
| Phenoxyethanol | 0.4 | 0.38 |
| Jaguar C13S | 0.1 | 0.095 |
| Perfume | 0.55 | 0.52 |
| Sodium benzoate | 0.5 | 0.48 |
| Sodium chloride | 1.0 | — |
| Propellant (CAP40) | — | 5 |
| Water, minors | q.s | q.s |

The formulation of Example 1 was prepared by simple blending of the ingredients, followed by sealing into a mousse can and charging with propellant to produce a mousse shampoo formulation.

For Comparative Example A, a high shear mixer was used during manufacture to produce a stable emulsified liquid (non-mousse) shampoo formulation.

The formulations were subjected to comparative testing on hair to evaluate their effect on smoothness, softness and ease of comb, using the following methodology:

Six 10 inch (7g) hair switches were balanced by washing in a base shampoo and running the panel test as described below to ensure that there were no significant differences between any of the switches. Three were then washed in the formulation of Comparative Example A and three in the formulation of Example 1 (1 g Comparative Example A or 0.6 g Example 1 per switch, 30 sec wash followed by 30 sec rinse followed by a repeat wash/rinse cycle). The mousse can of Example 1 was shaken before product was dispensed.

After combing out and drying, panellists were asked to compare pairs of switches for each of the three attributes. Each pair consisted of one switch from each group of three i.e. one washed with Comparative Example A and the other with Example 1. Each panellist made 6 different paired comparisons out of a possible total of 9 for the six switches. Twelve panellists were used making a total number of paired comparisons of 72. The test was balanced so that all pairs were tested an equal number of times. For each comparison the panellist voted for one switch, i.e. the one which displayed the attribute to the greatest extent. The results were analysed statistically against a hypothesis of equal preference (binomial probability =½). Tests for assessor consistency and switch consistency were also performed.

The results showed a clear win over all three properties (softness, smoothness and ease of comb) for the formulation of Example 1 over the formulation of Comparative Example A. This was particularly surprising in view of the fact that a lower dosage of Example 1 (0.6 g per switch) was applied to the switches in the test compared with Comparative Example A dosage (1 g per switch).

Example 2

A shower mousse formulation was made up using the following ingredients.

| Ingredient | Example 2 (wt %) |
|---|---|
| Sodium Laureth Sulfate | 7.60 |
| Disodium Laureth Sulfosuccinate | 2.55 |
| Lauryl Glucoside | 0.85 |
| Glycerin | 1.20 |
| Isopropyl Palmitate | 0.50 |
| Helianthus Annuus (Sunflower Oil) | 9.50 |
| Carbomer | 0.10 |
| Perfume | 1.15 |
| Preservative | 0.20 |
| Propellant | 6.00 |
| Water | q.s |

The formulation of Example 2 was prepared by simple blending of the ingredients, followed by sealing into a mousse can and charging with propellant to produce a shower mousse formulation.

What is claimed is:

1. A mousse-forming cleansing shampoo composition having improved conditioning performance comprising:
   (A) a foamable concentrate comprising:
      (i) at least one surfactant;
      (ii) dispersed particles of a water-insoluble conditioning agent having a particle size of 1 micron or greater;
      (iii) an aqueous carrier;

wherein the dispersed particles of water-insoluble conditioning agent are not suspended by a suspending agent, and (B) an aerosol propellant.

2. A composition according to claim 1, in which the conditioning agent is selected from the group consisting of silicones, high molecular weight hydrocarbon materials, hair conditioning oily or fatty materials and mixtures thereof.

3. A composition according to claim 1, in which the foamable concentrate further comprises a rheology modifier selected from the group consisting of polyethylene glycol (PEG), polypropylene glycol (PPG), sodium xylene sulphonate, sodium toluene sulphonate and urea.

4. A composition according to claim 1, in which the conditioning agent is selected from the group consisting of emulsified silicone, emulsified polyisobutylene resin, and mixtures thereof.

5. A composition according to claim 4, which further comprises a deposition polymer.

6. A composition according to claim 1, in which the conditioning agent is selected from the group consisting of hydrocarbon oils, fatty esters and mixtures thereof.

7. A composition according to claim 1, in which the propellant gas is selected from the group consisting of dimethyl ether, propane, n-butane, isobutane and mixtures thereof.

8. A composition according to claim 1, wherein the viscosity of the foamable concentrate is from 1 to 3000 cps.

9. A composition according to claim 1, wherein the viscosity of the foamable concentrate ranges from 10 to 2000 cps.

10. A composition according to claim 9, wherein the viscosity of the foamable concentrate ranges from 100 to 1000 cps.

* * * * *